United States Patent
Narang et al.

(10) Patent No.: US 6,323,042 B1
(45) Date of Patent: Nov. 27, 2001

(54) MICROCAPILLARY-BASED FLOW-THROUGH IMMUNOSENSOR AND DISPLACEMENT IMMUNOASSAY USING THE SAME

(75) Inventors: Upvan Narang, Raleigh, NC (US); Paul R. Gauger, Alexandria, VA (US); Frances S. Ligler, Potomac, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/435,833

(22) Filed: Nov. 8, 1999

Related U.S. Application Data (62) Division of application No. 08/845,894, filed on Apr. 28, 1997, now Pat. No. 6,020,209.

(51) Int. Cl.[7] .................................................. G01N 33/558
(52) U.S. Cl. .............................. 436/514; 422/55; 422/59; 422/82.08; 422/82.11; 435/7.1; 435/7.93; 435/7.94; 435/7.95; 435/287.7; 435/287.8; 435/287.9; 435/288.7; 435/808; 435/6; 436/164; 436/172; 436/518; 436/527; 436/535; 436/541; 436/805

(58) Field of Search .................... 422/55, 59, 82.08, 422/82.11; 435/7.1, 7.93, 7.94, 7.95, 287.7, 287.8, 287.9, 288.7, 808, 6; 436/164, 172, 518, 527, 535, 541, 514, 805

(56) References Cited

U.S. PATENT DOCUMENTS

| | | | |
|---|---|---|---|
| 5,183,740 | 2/1993 | Ligler et al. | 435/7.32 |
| 5,741,639 | 4/1998 | Ensing et al. | 435/6 |

*Primary Examiner*—Christopher L. Chin
(74) *Attorney, Agent, or Firm*—John J. Karasek; Amy L. Reasing (57) ABSTRACT

A displacement-type flow immunoassay is performed using a microcapillary passage. The inner wall of the microcapillary passage has immobilized thereon antibodies to the antigen of interest. Labeled antigen is immunologically bound to the immobilized antibodies. Sample antigen passing through the column displaces the labeled antigen. Downstream, the displaced labeled antigen is detected. The microcapillary format of the present invention enhances the sensitivity of the immunoassay over the sensitivity of displacement-type flow immunoassays performed in a column at similar flow rates.

9 Claims, 9 Drawing Sheets

MICROCAPILLARY-BASED FLOW-THROUGH IMMUNOSENSOR AND DISPLACEMENT IMMUNOASSAY USING THE SAME

This application is a divisional application of prior application Ser. No. 08/845,894, filed Apr. 28, 1997, now issued as U.S. Pat. No. 6,020,209 on Feb. 1, 2000.

BACKGROUND OF THE INVENTION

1. Field of the Invention

The present invention is related generally to immunosensors, and more specifically to immunosensors for flow-through displacement immunoassays.

2. Description of the Background Art

Immunoassays exist in a variety of formats that utilize the interaction of antibodies with antigens usually including direct binding, competitive and sandwich assay schemes. The continuous flow immunoassay is a unique displacement assay that measures the dissociation of a fluorescently labeled antigen from an antibody bound on a solid support when the antigen flows past the antibody (U.S. Pat. No. 5,183,740, issued Feb. 2, 1993 to Ligler et al., the entirety of which is incorporated herein by reference for all purposes.) The displacement of the labeled antigen is proportional to the quantity of antigen present in the sample. Sensitivity of the assay is dependent on the dissociation constant of the antibody and the probability of antigen-to-antibody interaction in the flow system.

In previous studies on flow immunoassays using columns of packed beads or porous membranes as substrates for the antibody immobilization, the following parameters have been determined to affect signal magnitude and assay sensitivity:

(1) The affinity of the antibody for the antigen must be as high or higher than the affinity of the antibody for the labeled analog under the conditions of operation of the displacement immunoassay.

(2) There is a minimum number of antibody-labeled antigen complexes that must be present in the assay in order to generate a signal. Past this minimum level, increasing the number of antibodies by increasing the amount of substrate or antibody density increases the signal magnitude and the number of assays that can be performed, but may decrease the antigen sensitivity, probably due to rebinding of labeled antigen to immobilized antibody. The minimum detectable amount of displaced labeled antigen is also a function of detector sensitivity.

(3) For each antigen-antibody pair, there seems to be an optimum flow rate which is probably related to the dissociation constant of the antibody. Increasing the flow rate above this level increases spontaneous dissociation of labeled antigen, decreases antigen-antibody interaction time, and, consequently decreases the displacement efficiency (ratio of the number of moles of antigen added vs. number of moles of labeled antigen displaced). Decreasing the flow rate too much results in poor discrimination of the signal from background due to peak broadening. In general, flow rates of 0.1 to 2.0 ml/min are taught with 0.2 to 1 ml/min being preferable (U.S. Pat. No. 5,183,740, infra). If not for an unacceptably low signal to background ratio, low flow rates would be desirable for the detection of low analyte concentrations in small (e.g., one picoliter to ten microliters) samples.

In Wemhoff et al. (Wemhoff, G. A., S. Y. Rabbany, A. W. Kusterbeck, R. A. Ogert, R. Bredehorst, and F.S. Ligler *J. Immunol. Methods*, 156, 223–230, 1992), the concept of displacement efficiency was introduced as means for comparing assay performance as various parameters were modified. The displacement efficiency is at its maximum when the concentration of antigen added is low relative to the dynamic range for the column being used. The amount of displaced labeled antigen molecules does not exceed the displacement efficiency times the concentration of labeled antigen bound to the immobilized antibody, even when high concentrations of antigen are added. For the packed bed columns, a maximum displacement efficiency of about 0.001 was typical under optimal flow conditions.

U.S. Pat. No. 5,183,740 to Ligler et al. teaches a variety of support media, including capillary tubes. That patent, however, attaches no criticality to the form of the support media or column. Moreover, that patent fails to teach a range of capillary inner diameters and lengths and fails to suggest any relationship between capillary diameter/length and sensitivity.

Finally, obtaining consistent results from sample to sample requires columns that can be manufactured consistently, reliably, and reproducibly. Packing columns with beads is an imprecise process that results in variability among columns.

SUMMARY OF THE INVENTION

Accordingly, it is an object of this invention to improve the sensitivity of a displacement-type flow immunoassay.

It is a another object of the present invention to reduce the amount of sample required for a displacement-type flow immunoassay.

It is a further requirement of the present invention to provide a flow immunoassay support that can be prepared easily and reproducibly.

It is yet another object of the present invention to provide a flow immunoassay support that can be used with integrated optics.

These and other objects are accomplished by a microcapillary-based flow immunoassay. An antibody is immobilized on the interior of a microcapillary tube. The available antigen-binding sites of the antibody are then immunologically bound to a labeled analog of the antigen. When a sample containing the antigen flows through the microcapillary tube, sample antigen displaces the labeled analog.

If the microcapillary functioned as a support for the displacement assay in the same manner as packed beads, the operational parameters for the packed bead columns would indicate that the microcapillary would not produce sufficient signal for measurement. Based on this displacement efficiency and the estimated number of labeled antigen molecules in the capillary, a maximum of $1.4 \times 10^{-18}$ moles of labeled antigen could be displaced at any one sample addition. (The amount of labeled antigen that can be displaced from the capillary is calculated based on the following assumptions: (1) As described for the antibody immobilization chemistry by Bhatia et al., *Anal. Biochem*, 178, 408–413, 1989), up to 0.66 nm/mm² antibody can be immobilized on borosilicate glass. The antibody can bind a small antigen in a 1:1 ratio. (2) The surface area of the capillary is 346 mm². (3) The antibody has a molecular weight of approximately 160,000, and (4) the displacement efficiency is 0.001. Thus, 346 mm²*(0.66) ng antibody/mm²) * 1 nmole antibody/160,000 ng)*(nmole labeled antigen/1 nmole antibody/mm²)*0.001=1.4 $\times 10^{-18}$ moles of labeled antigen.) Assuming no peak broadening, this amount of antigen in a 100 µl volume would produce a molarity of $1.4 \times 10^{-14}$, which would not be detected using a standard HPLC fluorimeter with a sensitivity to the label of approximately $10^{-11}$ molar. Nevertheless, as shown in the Detailed Description of the Preferred Embodiments below, the present invention actually provides enhanced sensitivity over prior art displacement immunoassays.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DESCRIPTION OF THE PREFERRED EMBODIMENTS

U.S. Pat. No. 5,183,740 to Ligler et al. describes the general characteristics of displacement immunoassays under flow conditions and is incorporated herein, in its entirety, by reference for all purposes.

A microcapillary tube useful according to the present invention has an inner diameter of no greater than about 1 mm. At diameters greater than about 1 mm, the unexpectedly large increase in sensitivity will not occur. There is no lower limit on the size of the inner diameter of the microcapillary, as long as the relevant sample will flow through it.

For each antigen-antibody pair, there seems to be an optimum flow rate that is related to the binding kinetics of the antibody. Increasing the flow rate above this level can both cause increased spontaneous dissociation of labeled antigen and decreased antigen-antibody interaction time. Decreasing the flow rate too much results in poor discrimination of the signal from background due to peak broadening. When comparing flow streams through microcapillaries of different sizes, however, it is more accurate to refer to linear flow velocity rather than flow rate.

For the detection of TNT using antibodies as described in the accompanying examples, the best results were obtained at linear flow velocities (flow rate/cross-sectional area of the microcapillary) of about 20 cm/min to about 105 cm/min. Flow velocities of less than 20 cm/min may provide equal or better results, but will require a pump capable of slower flow velocities than those used in the accompanying examples Although the optimum linear flow velocities for other antigen/antibody pairs may vary somewhat from those described for TNT above, the optimum flow velocities for many antigen/antibody pairs should be near those described above for TNT detection. In any event, a person skilled in the art of immunoassays should be able to determine the actual optimal flow velocity for any antigen/antibody pair determined empirically, without the exercise of inventive skill, based upon the teachings provided in the instant application.

The microcapillary tubes may be made from any material that does not absorb or change the chemical properties of the antigens, labels or antibodies used and is capable of immobilizing an antibody thereon. Typically, the microcapillary tubes are made of glass, but they may also be made, for example, from a polymer (such as polystyrene, polycarbonate, polyvinyl and polyacrylic) or ceramic.

Figure 1A:
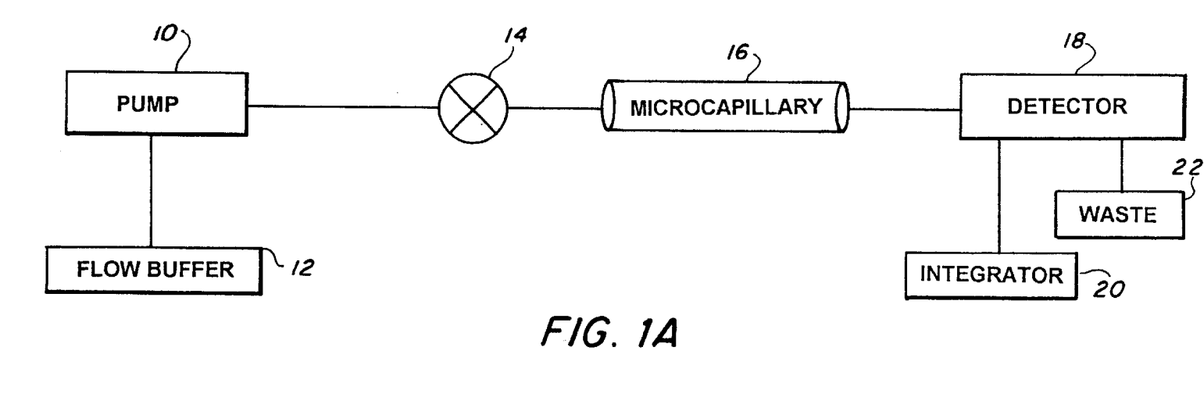
FIG. 1A is a simplified schematic of a microcapillary immunosensor according to an embodiment of the present invention.
Figure 1B:
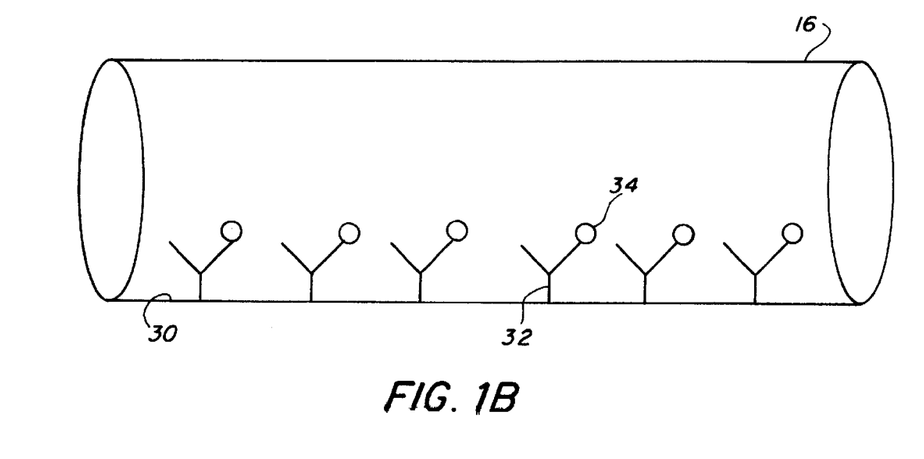
FIG. 1B is an expanded schematic view of a section of microcapillary from the immunosensor shown in FIG. 1A.

As shown in FIG. 1A, pump 10 delivers flow buffer 12 to injector 14. A liquid sample suspected of containing antigen is injected into flow buffer 12 by injector 14. From injector 14, the flow buffer/sample stream passes through microcapillary 16. As shown in FIG. 1B, inner walls 30 of capillary 16 have antibodies 32 immobilized (e.g., by covalent bonding) thereon. The antigen-binding sites of antibodies 32 are effectively saturated (i.e., the binding sites are at least sufficiently close to saturation with labeled analog molecules that the microcapillary essentially behaves as though the binding sites were completely saturated. Throughout the present specification and claims, the term "saturated" encompasses "effectively saturated" unless otherwise stated) with labeled analog 34 of the antigen of interest. Within microcapillary 16, unlabeled antigen, if present, displaces labeled analog 34 into the stream of flow buffer 12. Downstream of microcapillary 16, detector 18 detects displaced labeled analog 34. The signal from detector 36 is then fed into integrator 20, which integrates these signals. The integrated signal may then be recorded. Waste fluid containing the sample and displaced labeled analog 34 are then collected or drained into waste disposal 22.

The present invention may also be adapted to simultaneously test several samples and/or to test one sample for a plurality of antigens. In these embodiments, a single pump and flow buffer stream are connected in parallel to several microcapillary tubes, each microcapillary tube having its inside surface coated with an antibody to a specific antigen of interest, the antibodies coated on the inside surface of each microcapillary tube having their antigen binding sites saturated with a labeled analog of the corresponding antigen.

The small diameter of the microcapillary tubes used in the present invention allows for another novel immunoassay format. In is this new format, microcapillary passages, as well as an entrance and exit for flow buffer, are molded or micro-machined into a monolithic substrate such as a chip or cartridge. If desired, the microcapillary passages may be coiled or serpentine. The chip/cartridge may be made from any material, for example, silicon or other semiconductor, polymer, or glass, that is neutral to the materials being analyzed, and that can be readily machined or molded to form microcapillary passages therein having inner walls capable of immobilizing an antibody. If desired, an electroosmotic pump may be used to flow fluid through the microcapillary or microcapillaries in the chip/cartridge (see Effenhauser, C. S., A. Manz, and H. M. Widmer. *Analytical Chemistry*. 67, 2284–2287, 1995.; Jacobson, S. C. and J. M. Ramsey. *Analytical Chemistry*, 68, 720–723, 1996). The entireties of each of these papers are incorporated herein by reference for all purposes). Alternatively, pneumatic pumps or mechanical and valves could be used for fluid control and still produce a small, lightweight flow immunosensor.

After machining or molding, the inner passages of the chip/cartridge are then coated with antibody molecules immobilized thereon. The antigen binding sites of these immobilized antibodies are then saturated with a labeled analog of the antigen. The finished assembly may then be inserted into an receptacle designed so that the entrance port of the chip/cartridge aligns and forms a releasable fluid-tight seal along a flow path for buffer downstream of a sample injector and upstream from a detector. If a detection cell/cuvette is external (i.e., in the receptacle) to the chip, the exit port of the chip/cartridge should also align with and form a releasable fluid-tight seal with the flow path upstream from the detection cell/cuvette, but downstream from the entrance port. Where the detection cell is integrated with the chip, the exit port may be in fluid connection with the microcapillary passage, downstream of the entrance port, and should drain spent buffer and label away from the receptacle, or at least away from components of the receptacle that may not be readily cleaned or replaced. Buffer flow through the microcapillary passage(s) is then established. Thereafter, sample is injected into the buffer flow and enters the microcapillary passage(s) in the chip/cartridge. After exiting the microcapillary passage, buffer flow and displaced labeled analog flow downstream into the detector. The detector may be integrated into the chip/cartridge, or positioned downstream from the chip/cartridge. After the assay has been completed, the chip/cartridge may be readily removed and a new chip/cartridge inserted. This embodiment forms a particularly useful arrangement for field use.

Figure 1C:
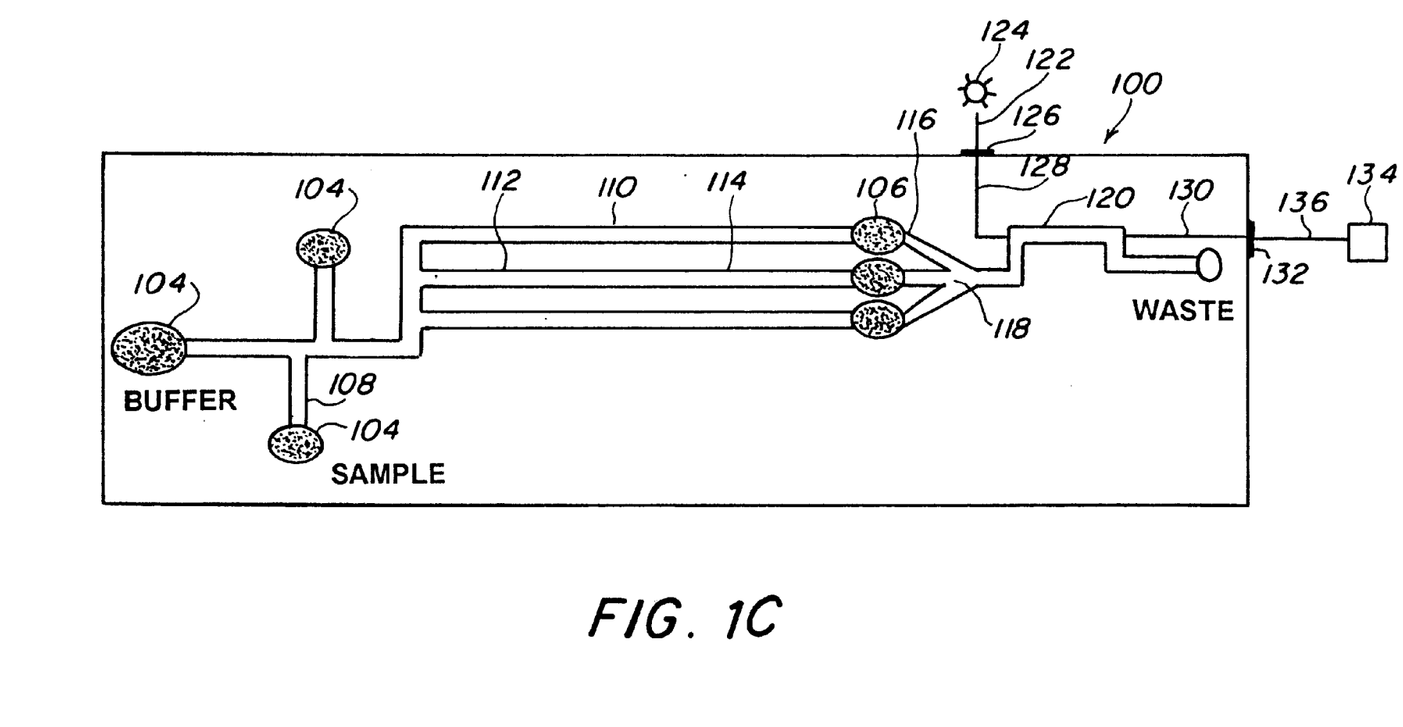
FIG. 1C is a simplified schematic of a microcapillary immunosensor on a chip according to another embodiment of the present invention.

FIG. 1C shows a flow immunosensor chip 100. Buffer flow through microcapillary passage 102 by virtue of an electroosmotic gradient generated by electrodes 104 and oppositely charged electrodes 106. Sample port 108 connects to microcapillary passage 102, allowing a liquid sample to be introduced into microcapillary passage 102. Downstream of sample port 108, microcapillary passage 102 divides into three daughter microcapillary passages 110, 112, and 114. Each of these three daughter passages 110, 112, and 114 has, immobilized on its inner surface, a coating of an antibody that has its antigen recognition sites saturated with a labeled analog of an antigen of interest. The antibody/antigen pairs and labels used may be the same for each daughter passage, or may differ among the daughter passages. Further downstream, at point 116, the inner coatings along the daughter passages terminate. Downstream of point 116, daughter passages 110, 112, and 114 rejoin to form passage 118 leading into detection cell/cuvette 120 (A chip cuvette is disclosed in, for example, Liang, Z., N. Chiem, G. Ocvirk, T. Tang, K. Fluri, and K. J. Harrison. *Analytical Chemistry*, 68, 1040–1046, 1996, the entirety of which is incorporated herein by reference for all purposes). The detection includes at least one window transparent to excitation light and at least one window transparent to the fluorescent emissions of the excited label.

Optical fiber 122 transports excitation light from light source 124 (for example, an LED) to optical fiber 128 through releasable coupler 126. A simple butt coupling (not shown) may be used rather that couple 126. Optical fiber 128 transports the excitation light to detection cell 120. The excitation light causes any displaced labeled analog in detection cell 120 to emit fluorescent light. Optical fiber 130 transports this fluorescent emission to detector 134 through releasable coupler 132 and optical fiber 136. Appropriate filters for the excitation light and fluorescent emissions may be added at any point along the respective light paths. For example, filters may be incorporated into the ends of detection cell 120, between light source 124 and optical fiber 122, and/or between detector 134 and optical fiber 136. Releasable couplers 126 and 132 are designed to optically couple fibers pairs 122/128, and 130/136, respectively, when chip 100 is inserted into its receptacle (not shown). Power for an electroosmotic pump or other fluid pump, as well as any other on-chip components, may be provided by a battery incorporated into the chip or external to the chip.

In the embodiment shown in FIG. 1C, the light source and detector, and associated circuitry for those components, are included in a receptacle external to the chip. That arrangement decreases the cost of the chip, making the disposability of the chip highly practical. If desired, however, an LED, and any appropriate filters, may be incorporated into the chip as the light source, and a photodiode, and any appropriate filters, may be provided as the detector. Data from a detector internal to the chip could be ported to a recording device and/or computer via, for example, an RS232 port built onto the chip. The circuitry for each of these components may be provided on the chip. The cost of these additional on-chip components and their required circuitry, of course, significantly adds to the expense of the chip.

Having described the invention, the following examples are given to illustrate specific applications of the invention including the best mode now known to perform the invention. These specific examples are not intended to limit the scope of the invention described in this application.

EXAMPLES

Example 1
Displacement Immunoassay in a Microcapillary

The following materials, equipment, and methods were used in all examples, unless otherwise stated:

Materials. Fused silica microcapillaries (Polymicro Technologies, Inc.); 3-mercaptopropyltrimethoxysilane (MTS), N-succinimidyl-4-maleimidobutyrate (GMBS; Fluka); ethanol (200 proof; Warner-Graham); toluene (Mallinkrodt); tween, (Sigma); sodium monophosphate (Aldrich); 2,4,6-trinitrotoluene (TNT), and 1,3,5-trinitrobenzene (TNB). Anti-TNT antibody 11B3 was generated at NRL and another anti-TNT antibody was purchased from Strategic Diagnostics, Inc. All reagents were used as received without further purification and aqueous solutions were prepared in doubly distilled deionized water unless otherwise noted.

Equipment. FIG. 1A schematically illustrates the microcapillary-based continuous flow immunosensor used in these examples. A Rabbit-Plus peristaltic pump (Rainin Instruments), a low pressure Rheodyne five-way valve sample injector, a Model 821-FP spectrofluorometer (Jasco, Inc.), and a HP33936B Series II integrator (Hewlett-Packard) were used. A model HP-9114B disc drive (Hewlett-Packard, Inc.) was utilized to store analog output data from the fluorometer for subsequent analysis. All connecting tubes were 0.3-mm-i.d. Teflon (Cole Palmer).

Flow Buffer. The flow buffer comprised of a mixture of sodium monophosphate (10 mM), ethanol (2.5%), and Tween-20 (0.01%, Aldrich). All solutions to be analyzed using the microcapillary immunosensor were prepared in the flow buffer.

Antibody immobilization in a microcapillary. Antibodies were immobilized on the inner walls of the microcapillaries essentially according to the method of Bhatia, S. K., L. C. Shriver-Lake, K. J. Prior, et al. (*Anal. Biochem*, 178, 408–413, 1989). A desired length of fused silica microcapillary (0.80 or 0.55 mm i.d.) was incubated with a 4% MTS solution (in toluene) at room temperature for one hr. After flushing the microcapillary with toluene 3 times, a 2 mM crosslinker solution (GMBS) was introduced in the microcapillary and incubated at room temperature for 1 hr. The microcapillary was then rinsed with deionized water. A 1 mg/ml solution of anti-TNT antibody 11B3 or Strategic Diagnostics anti-TNT antibody was introduced into the microcapillary for 1 hr. The microcapillary was then rinsed with water 3 times. Finally, a 30 $\mu$M Cy5-trinitrobenzene (Cy5-TNB; synthesized as previously described (Bart, J. C., L. L Judd, K. E. Hoffman, A. M. Wilkins, P. T. Charles and A. W. Kusterbeck, *ACS Symposium Series*, in press) solution was introduced into the microcapillary and incubated in a refrigerator at 4° C. for about 8 to 12 hours. (No attempt was made to determine the minimum useful incubation time. Far shorter incubation times than those used in the present examples may be empirically determined to provide equivalent results)

Immunoassay. The flow buffer was pumped through the microcapillary at the desired flow rate and the fluorescence of the Cy5-TNB was monitored downstream using the fluorometer equipped with a 16 $\mu$L flow cell. Unless otherwise stated, the microcapillary was 20 cm long with a 0.55 mm i.d. and was run at a flow rate of 0.2 ml/min (linear flow velocity=84 cm/min). The excitation wavelength used was 632±4 nm and the fluorescence emission was monitored at 662±4 nm. Initially, there was a constantly changing slope for background fluorescence intensity as a function of time indicating the washing of the excess and nonspecifically adsorbed Cy5-TNB from the walls of the microcapillary. After approximately 30 min, the background fluorescence stabilized, i.e. a constant rate for change in fluorescence intensity was achieved. At this point, 100 $\mu$L injections of flow buffer containing 0–500 ng/mL TNT were made. The resulting peaks due to the displacement of the fluorescently-labeled antigen were recorded and the area under the peaks was quantified. Injections at each concentration were made in triplicate.

Figure 2A:
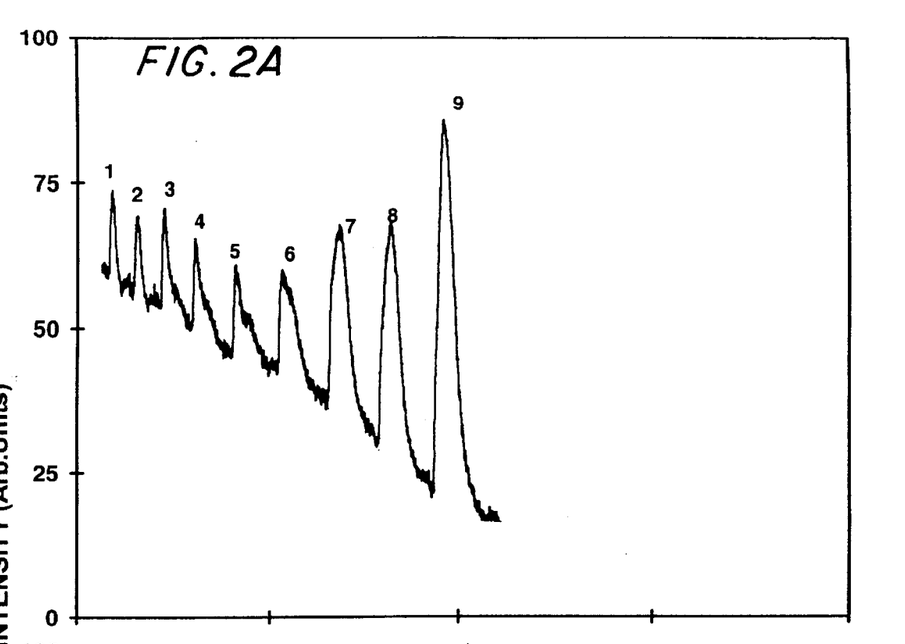
FIG. 2A shows peaks due to displacement of Cy5-TNB upon injecting 100 µL of variable concentrations of TNT solution on an anti-TNT antibody 11B3-coated microcapillary immunosensor (0.55 mm i.d.; 20 cm long). Injections 1–9 correspond to a TNT concentration of 0.25, 0.5, 1, 5, 25, 50, 125, 250,and 500 ng/mL, respectively.
Figure 2B:
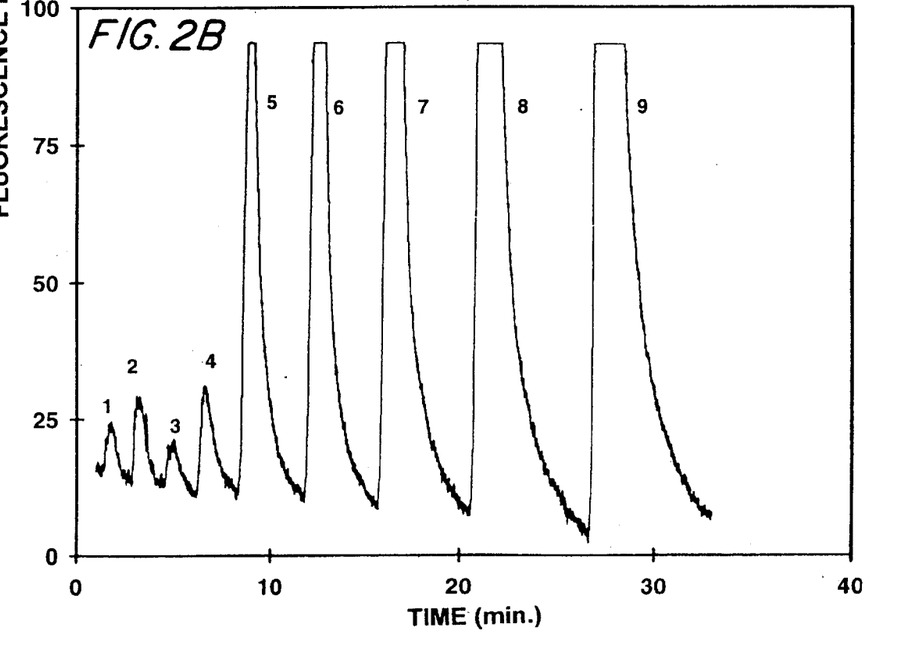
FIG. 2B shows peaks resulting due to displacement of Cy5-TNB upon injecting variable concentrations of TNT solution on an anti-TNT antibody-coated microcapillary immunosensor (0.55 mm i.d.; 20 cm long). Injections 1–9 correspond to a TNT concentration of 0.15, 0.3, 0.15, 6.25, 62.5, 125, 250, 500,and 1000 ng/mL, respectively.
Figure 3:
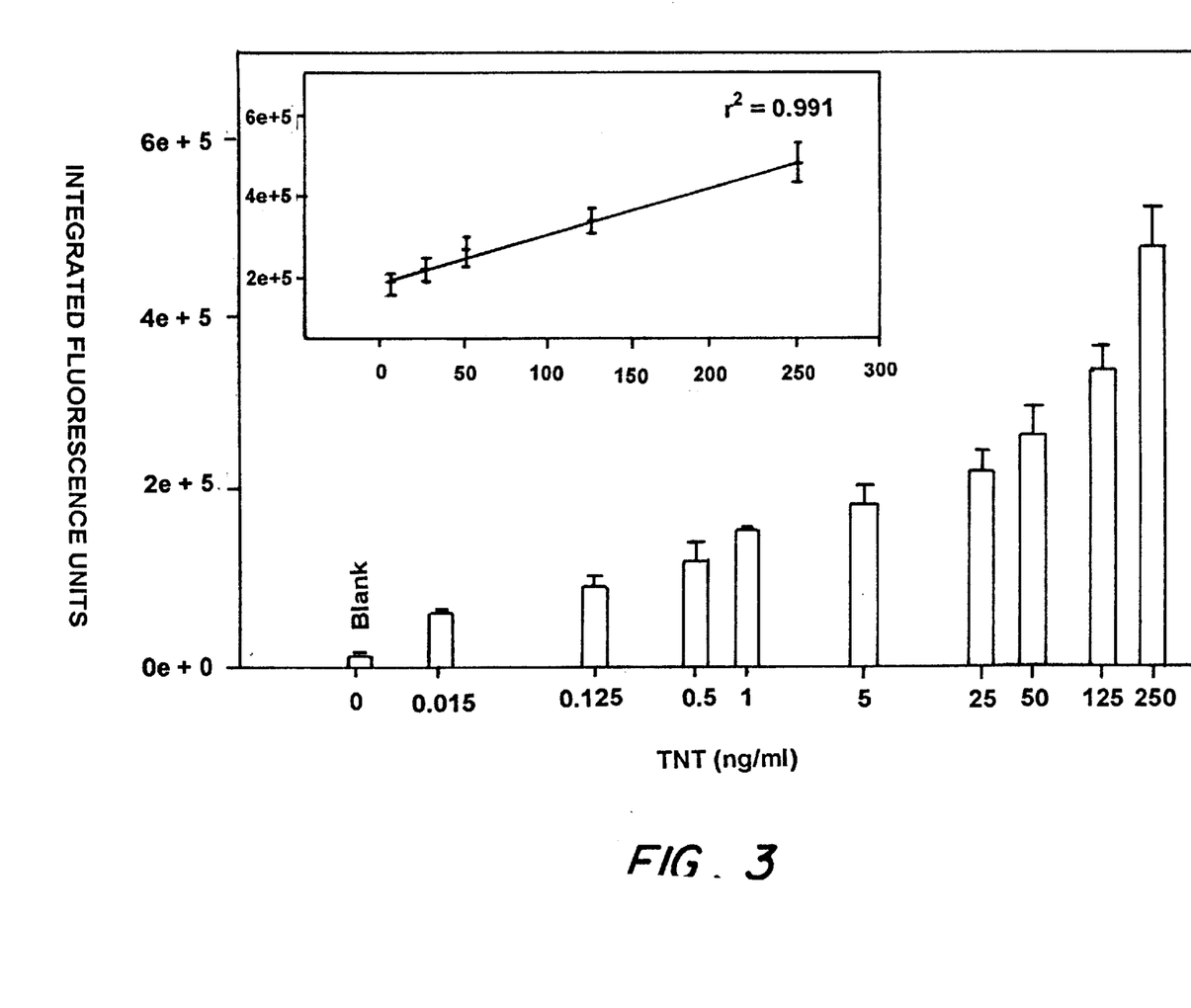
FIG. 3 is a graph showing the mean integrated area ± S.E. (triplicate samples) obtained upon injecting 100 µL at variable concentrations of TNT solutions to an anti-TNT 11B3 antibody-coated microcapillary immunosensor (0.8 mm i.d.; 20 cm long). The inset represents the linear dynamic range for TNT assay using the anti-TNT 11B3 antibody-coated microcapillary immunosensor.

FIG. 2A and FIG. 2B represent the resulting peaks upon injecting TNT at various concentrations (0.015–1000 ng/mL) to an anti-TNT antibody 11B3 coated microcapillary (FIG. 2A) and a Strategic Diagnostic anti-TNT-coated microcapillary (FIG. 2B). Injections 1–9 in FIG. 2A correspond to a TNT concentration of 0.25, 0.5, 1, 5, 25, 50, 125, 250, and 500 ng/mL, respectively. Injections 1–9 in FIG. 2B correspond to a TNT concentration of 0.15, 0.3, 0.15, 6.25, 62.5, 125, 250, 500, and 1000 ng/mL, respectively. FIG. 3 shows the mean integrated area ±S.E. of triplicate assays resulting from displacement of Cy-TNB from the 11B3 coated microcapillary immunosensor upon injecting varying concentrations of TNT. These results clearly demonstrate that: (1) microcapillary biosensor has a limit of detection which is at least three orders of magnitude better than packed bead (U.S. Pat. No. 5,183,740) and membrane based continuous flow immunosensors ("Displacement Assay on a Porous Membrane" F. S. Ligler, A. W. Kusterbeck, and S. Y. Rabbany, U.S. application); (2) there is a much higher displacement of labeled antigen observed for Strategic Diagnostic anti-TNT coated microcapillary immunosensor compared 11B3 coated microcapillary which is consistent with our ELISA results; and (3) under the current experimental conditions, the linear dynamic range is between 1–250ng/mL (FIG. 3 inset).

Example 2
Effect of Microcapillary Diameter

The effect of microcapillary diameter was studied using a 14 cm (0.80 mm i.d.) and a 20 cm (0.55 mm i.d.) microcapillaries which were coated with 11B3 anti-TNT antibody using the immobilization protocol explained above. The length of the two microcapillaries was kept such that the total surface area available for antibody immobilization is constant (346 mm$^2$). The limit of detection for TNT using both the microcapillaries was then determined. The linear flow velocity for the two microcapillaries was kept constant. It was observed that the limit of detection for the 0.8 mm i.d. microcapillary was 15 pg/mL and that for 0.55 mm i.d. microcapillary was 1 pg/mL. This experiment clearly demonstrates that the sensitivity of the system is dependent on the diameter of the microcapillary used. In this example, microcapillaries with i.d. lower than 0.55 mm could not be used because a continuous flow at lower flow rates could not be achieved using our peristaltic pump. This is a limit of the current experimental set up but in principle, smaller i.d. microcapillaries should work better.

Example 3
Effect of Flow Rate

Figure 4A:
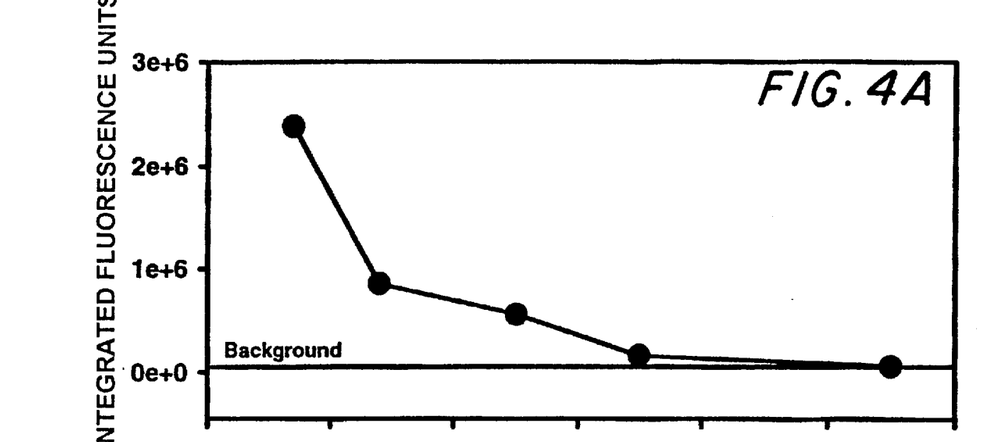
FIG. 4A, FIG. 4B, and FIG. 4C show, respectively, the integrated area, peak maxima, and full width at half maximum (FWHM) of the resulting peaks obtained upon injecting 100µL of 1 pg/mL TNT solution to a anti-TNT antibody-coated microcapillary immunosensor (0.55 mm i.d., 20 cm) as a function of the flow rate (µL/min) of the flow buffer.
Figure 4B:
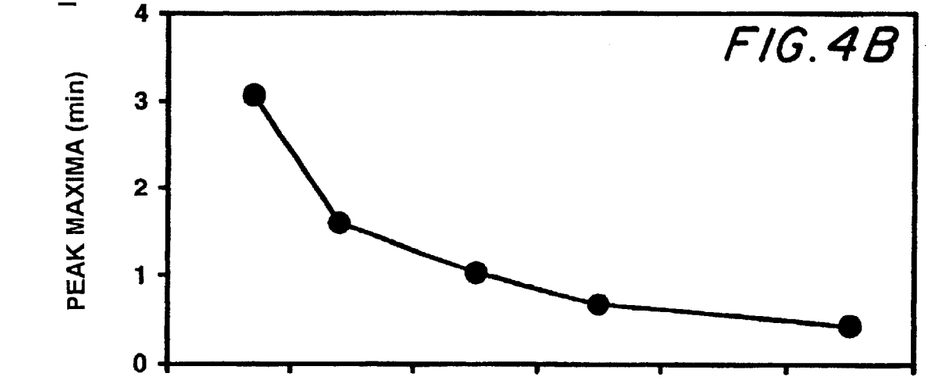
Figure 4C:
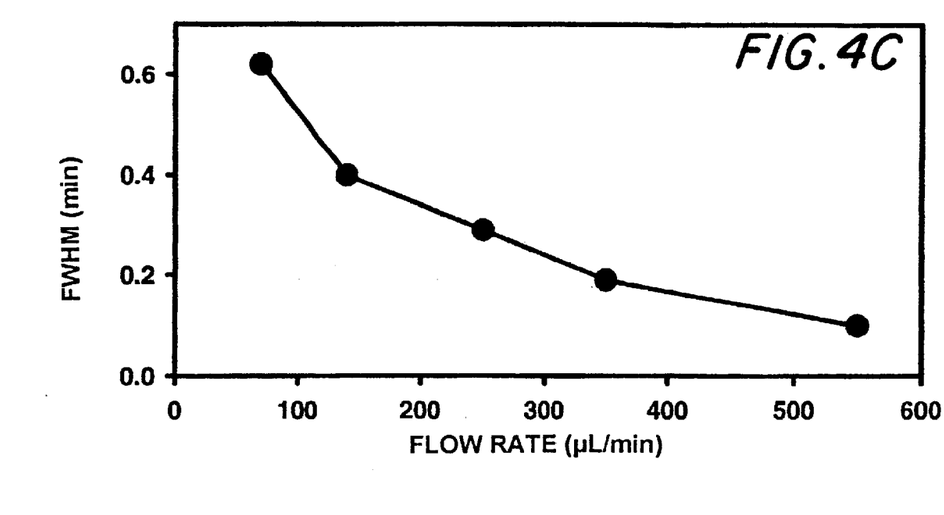

The effect of the flow rate was investigated using the 0.55 mm i.d. microcapillary (20 cm long). The flow rates ranged from 0.05 to 0.55 ml/min (linear flow velocity range=21 cm/minute to 231 cm/minute). FIG. 4A, FIG. 4B, and FIG. 4C represent the performance of the Strategic Diagnostic anti-TNT-coated microcapillary immunosensors as a function of the flow rate upon injecting 100 μL of 1 pg/mL TNT solution. FIG. 4A demonstrates that the signal magnitude produced by the microcapillary is highly dependent on the flow rate. Not only the fluorescence intensity but also the peak maxima (FIG. 4B) and full width at half maximum of the resulting peaks (FIG. 4C) are also affected by the flow rate. The concentration tested, 1 pg/ml, can be detected at flow rates less than 100 μL/min (linear flow velocity=42 cm/min), but is below the limit of detection for faster flow rates.

Example 4
Effect of Microcapillary Length.

Figure 5:
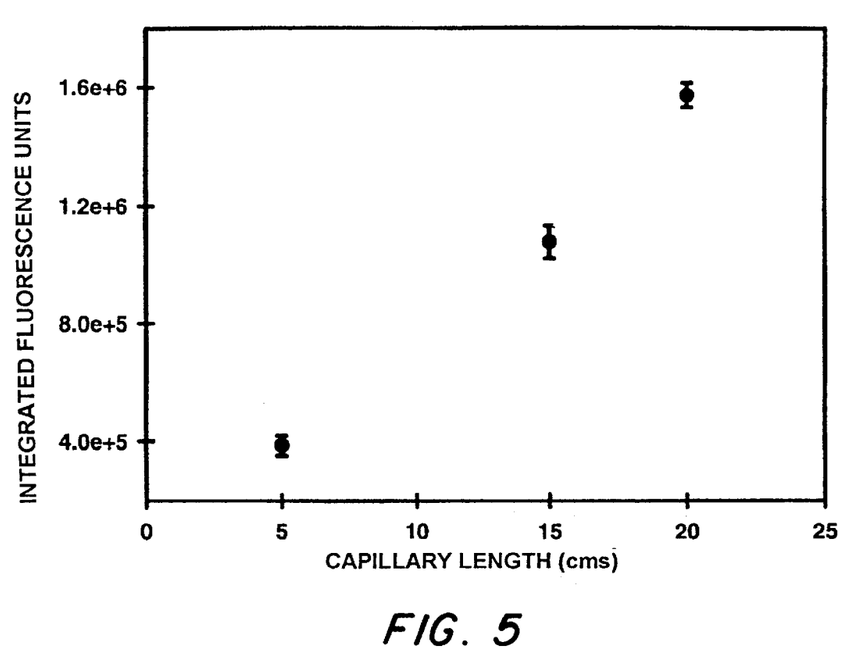
FIG. 5 shows the mean integrated area ±S.E. (triplicate samples) of the peaks obtained upon injecting 100 µL of 5 ng/mL TNT solution to an anti-TNT antibody-coated microcapillary immunosensor (0.55 mm i.d., 20 cm) as function of the length of the microcapillary.

The effect of length of the microcapillary was investigated by comparing the response of Strategic Diagnostic anti-TNT antibody coated 0.55 mm i.d. microcapillary as function of the length of the microcapillary. The linear flow velocity in all cases was kept constant at 190 μL/min (linear flow velocity=80 cm/min). FIG. 5 represents the integrated area of the peaks upon injecting 100 μL plugs of 5 ng/mL TNT solution to the microcapillary immunosensor. The magnitude of the displacement signal is dependent on the length of the microcapillary.

Example 5
Antigen quantitation

Figure 6:
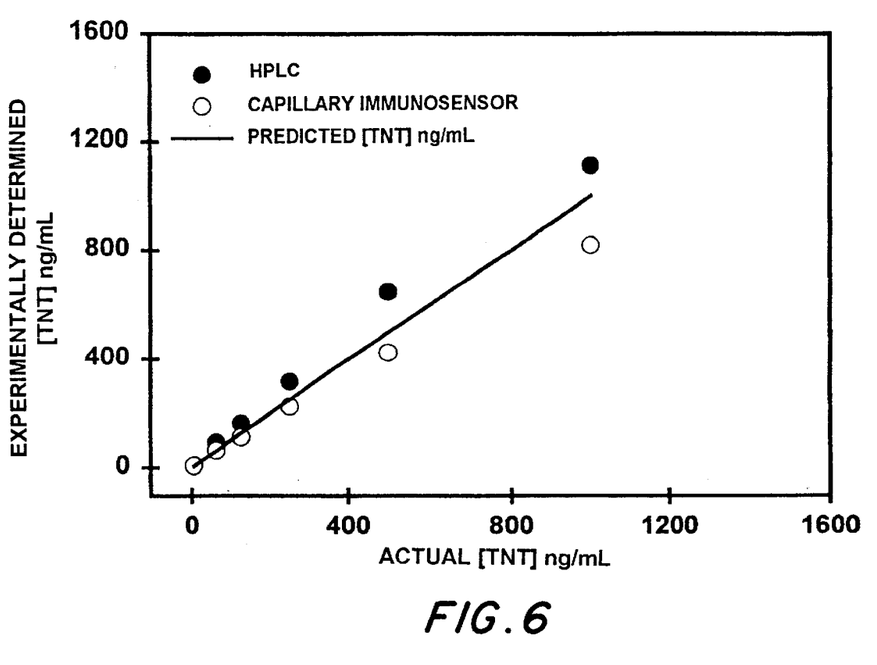
FIG. 6 shows the integrated area under the peaks obtained upon injecting variable concentration of TNT solution through an anti-TNT antibody-coated microcapillary immunosensor (α) (0.55 mm i.d., 20 cm) and a HPLC column (•). The solid line represents the actual concentration of the TNT solution prepared via diluting a stock TNT solution which was injected in either system.

In order to investigate the viability of this system for the quantitation of antigen, we compared the results of TNT spiked samples obtained by our microcapillary immunosensor and EPA method 8330 (HPLC method). For this experiment, a 1000 ng/mL stock TNT solution was prepared in the flow buffer. One portion of the stock TNT solution was diluted using the flow buffer for microcapillary immunosensor quantitation and the other portion was diluted using the mobile phase used for the HPLC. FIG. 6 is a plot of the results obtained using the microcapillary immunosensor (●) and HPLC method (○) as function of the actual concentration of TNT prepared using the stock TNT solution. The line is a reference line indicating a 100% correlation between the experimental results and the actual TNT concentration.

There are a few issues not apparent in FIG. 6 which require additional discussion. First, the limit of detection for the EPA 8330 HPLC method is 5 ng/mL whereas for the microcapillary immunosensor, it is 1 pg/mL. Second, up to 300 ng/mL, the correlation between the actual and experimentally determined TNT concentration is better for the microcapillary immunosensor compared to EPA 8330HPLC method. Third, there is a negative bias for the microcapillary immunosensor for concentrations above 300 ng/mL which is attributed to a reduction in displacement immediately after a large displacement. It should be noted that one can theoretically correct for the reduced displacement as described in Rabbany et al. (Rabbany, S. Y., A. W. Kusterbeck, R. Bredehorst, and F. S. Ligler, *Sensors & Actuators B*, 29, 72–78, 1995.) or Yu et al. (Yu, K., A. W. Kusterbeck, J. P. Whelan, M. Hale and F. S. Ligler, *Biosensors and Bioelectronics*, 11, 725–734, 1996.).

Example 6
Displacement Efficiency

This example investigated the displacement efficiency ($D_e$) of the microcapillary- and packed column-based continuous flow immunosensors. $D_e$ is defined as:

$$D_e = \frac{\text{moles of } Ag^* \text{ detected}}{\text{moles of } Ag \text{ injected}}$$

where Ag* and Ag represent the Cy5-TNB and TNT, respectively. Using microcapillaries 0.80 mm i.d. and 20 cm long, the displacement efficiencies of the Strategic Diagnostic and 11B3 anti-TNT antibody-coated microcapillaries were measured to be 0.8 and 0.4,respectively. In contrast, the displacement efficiency of a packed column-based displacement continuous flow immunosensor using the 11B3 anti-TNT antibody was measured at 0.0011. It should be noted that the calculated amount of antibody immobilized on the microcapillary and packed column were 0.002 nmoles[1] and 3.1 nmoles[2], respectively. Three points are clear from this study; (1) Strategic Diagnostic anti-TNT antibody microcapillary is more efficient by a factor of 2 compared to the 11B3 anti-TNT antibody coated microcapillary immunosensor, (2) the microcapillary immunosensor is more than 2 orders of magnitude more efficient than the packed column immunosensor, and (3) the microcapillary immunosensor requires much less antibody to generate a signal.

[1]Using the same assumptions as in footnote 1 and the appropriate microcapillary dimensions: 503 mm$^2$*(0.66 ng antibody/mm$^2$) * (1 nmole antibody/160,000 ng)=0.002 nmoles antibody.
[2]The beads in the packed column weighed 65.6 mg (mean of 3 columns). To each gram of beads, 7.6 mg of antibody was immobilized according to a previously described method (Yu et al., ibid.). Thus there are 3.1 nmoles antibody per column [0.0656 g beads*(7,600,000 ng antibody/g beads)*(1 nmole antibody/160,000 ng antibody)].

Example 7
Simultaneous Detection of Two Different Analytes

This example demonstrated that the capillary immunosensor format is suitable for use in the development of a multianalyte detection system. Toward this end, two capillaries were connected in parallel using a "T" connector and the simultaneous detection of two explosives, TNT and RDX, was demonstrated. Specifically, two capillaries, one coated with antibodies specific for 2,4,6-trinitrotoluene (TNT) and the other specific for hexahydro-1,3,5-trinitro-1,3,5-triazine (RDX) were combined into a single device to develop a multianalyte capillary flow immunosensor. The fused silica capillaries were prepared by coating anti-TNT and anti-RDX antibodies onto the silanized inner walls using a heterobifunctional crosslinker. After immobilization, the antibodies were saturated with a suitable fluorophore-labeled antigen. A "T" connector was used to continuously flow the buffer solution through the individual capillaries. To perform the assay, an aliquot of TNT, RDX, or a mixture of the two analytes was injected into the continuous flow stream. In each capillary, the target analyte displaced the fluorophore-labeled antigen from the binding pocket of the antibody. The labeled antigen displaced from either capillary was detected downstream using two portable spectrofluorimeters. Such a multianalyte approach also offers an on-line test for cross-reactivity.

Figure 7A:
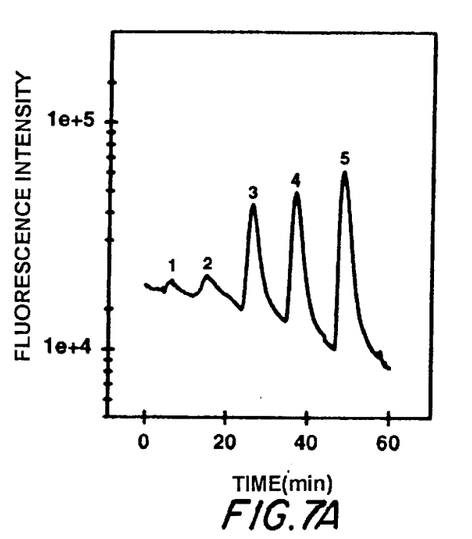
FIG. 7A is a graph of fluorescence intensity vs. time resulting from displacement of Cy5-TNB from the TNT capillary. Injections 1–5 correspond to a TNT concentration of 0.5, 5, 25, 50, and 250 ng/ml, respectively.
Figure 7B:
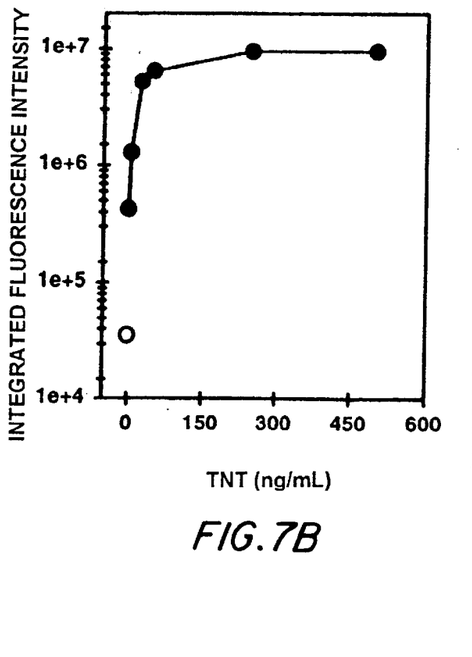
FIG. 7B shows a standard curve (integrated fluorescence intensity vs. concentration) for TNT in flow buffer using the multi analyte capillary flow immunosensor system.
Figure 7C:
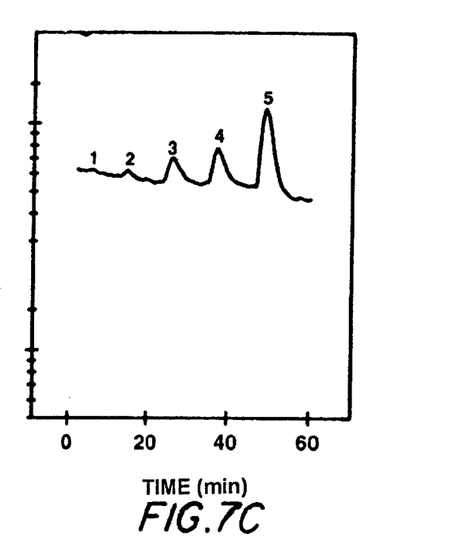
FIG. 7C is graph of fluorescence intensity vs. time resulting from displacement of Cy5-RDX from the RDX capillary. Injections 1–5 correspond to a RDX concentration of 0.5, 5, 25, 50,and 250 ng/ml, respectively.
Figure 7D:
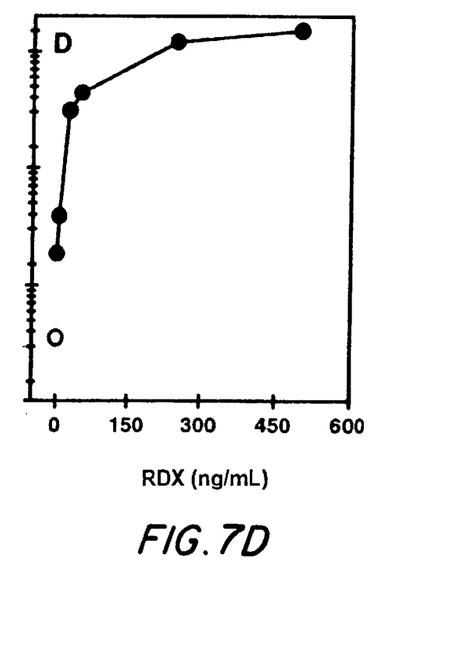
FIG. 7D shows a standard curve (integrated fluorescence intensity vs. concentration) for RDX in flow buffer using the multianalyte capillary flow immunosensor system.

FIG. 7A through FIG. 7D represents the resulting peaks (FIG. 7A and FIG. 7C) and the integrated fluorescence intensity (FIG. 7B and FIG. 7D) upon injecting a mixture of RDX and TNT prepared in flow buffer at various concentrations (0.5–500 ng/ml) into the multianalyte capillary flow immunosensor system. FIG. 7A (TNT capillary) and 7C (RDX capillary) represent the resulting peaks upon injecting a mixture of TNT and RDX to the MCFI system. We also injected mixtures of TNT and RDX at lower concentrations (<0.5 ng/ml) and observed that the limit of detection for TNT and RDX in the multianalyte format at 100 μl/min flow rate were 0.1 and 0.5 ng/ml, respectively. In both cases, there was a loss in sensitivity by a factor of 5 compared to the individual capillary immunosensors described in an earlier section. This loss in sensitivity was attributed to the dilution and peak broadening effect upon incorporating a "T" connector and other tubing connections in order to direct the flow into the two individual capillaries. This loss is a limitation of the experimental set up and with better connection tubing of low dead volume, the sensitivity can be improved. FIG. 7B and FIG. 7D represent the dynamic range of the TNT and RDX in the multianalyte format. As observed in the individual capillary immunoassay, there was a linear dependency on the concentration of TNT ($r^2$=0.95) and RDX ($r^2$=0.96) up to 100 and 300 ng/ml, respectively, after which the signal saturated in both cases.

Figure 8A:
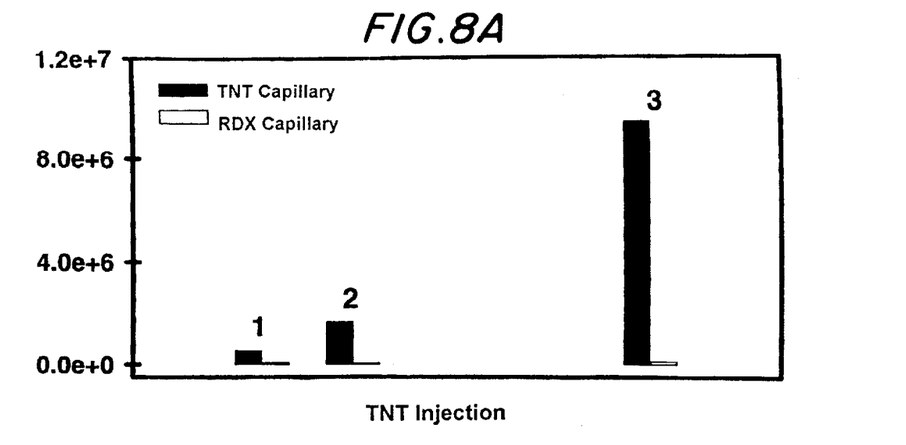
FIG. 8A shows the integrated fluorescence units of the area under the peaks in the TNT (■) and RDX (□) capillaries resulting from injecting 5, 50, and 10,000 ng/ml of TNT into the multianalyte capillary flow immunosensor system.
Figure 8B:
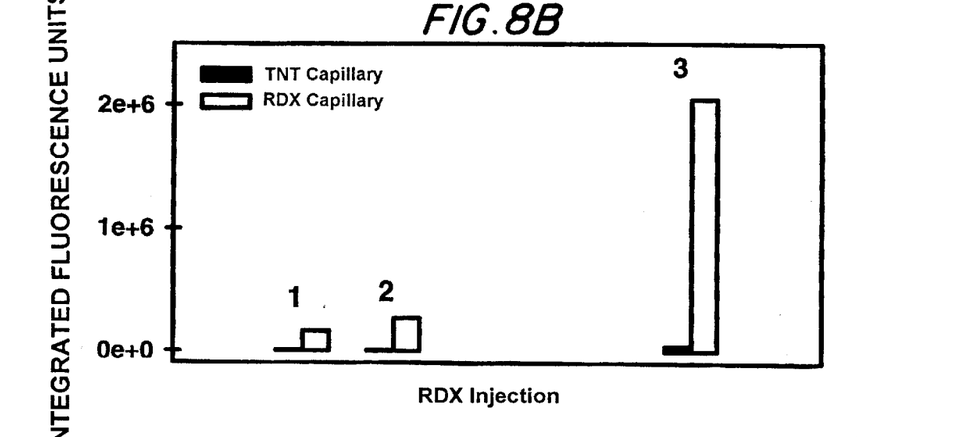
FIG. 8B shows the integrated fluorescence units of the area under the peaks in the TNT (■) and RDX (□) capillaries resulting from injecting 5, 50, and 10,000 ng/ml of RDX into the multianalyte capillary flow immunosensor system.
Figure 8C:
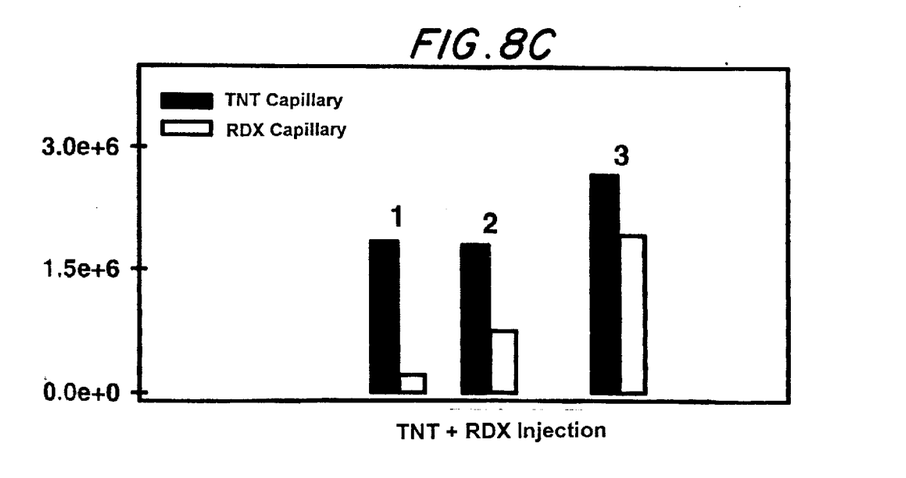
FIG. 8C shows the integrated fluorescence units of the area under the peaks in the TNT (■) and RDX (□) capillaries resulting from injecting mixtures of TNT and RDX at various concentrations into the multianalyte capillary flow immunosensor system; Injections 1, 2, and 3 correspond to a 100:100, 100:500, and 150:5000 ng/ml mixture of TNT:RDX, respectively. Assay conditions: flow rate=100 µl/min; injection volume=200µl; capillary i.d.=0.55 mm; capillary length=20 cm.

A very important feature of a multianalyte sensor is the crossreactivity of multiple antigens with the immobilized antibodies. In order to investigate this issue, first injected TNT was first injected only in to the multianalyte capillary flow immunosensor system and observed less than 1% displacement from the RDX capillary compared to the signal from the TNT capillary (FIG. 8A). Upon injecting RDX only to the multianalyte capillary flow immunosensor system, less than 1% signal was observed in the TNT capillary compared to the signal from the RDX capillary FIG. 8B). Finally, mixtures of TNT and RDX were injected and displacement from both the capillaries was observed (FIG. 8C). These results demonstrate that there is minimal cross-reactivity for the two antigens in the multianalyte capillary flow immunosensor system, so that it is an effective means of analyzing samples containing mixtures of TNT and RDX.

Example 8

Capillary Flow Immunoassay in Very Small i.d. Capillaries

As mentioned in the example 2, it was not possible to use capillaries smaller than 0.55 mm i.d. because of the peristaltic pump used. In order to achieve a continuous flow in the smaller i.d. capillaries (0.05 mm), a syringe pump was used. For very efficient excitation and fluorescence collection, the experimental set up under sheath flow conditions as described by Cheng et al., *Anal. Chem.* 1990, 62, 496–503, was used. Briefly, fluorescence was measured downstream from the column using a 635 nm laser (2.5 mW) for excitation and detecting the fluorescence signal using a 682±11 nm band pass and a photomultiplier tube (PMT).

Anti-TNT antibody/Cy5-TNB complex was immobilized onto the inner walls of 0.05 mm i.d. capillaries using the same protocol as used for the larger diameter capillaries described in an earlier section. Flow buffer was continuously flowed through the capillary using a syringe pump at a flow rate of 680 nl/min. Injections of 1.5 nl of TNT (concentration ranging from 1–10,000 ng/ml) were made into the capillary. Based on preliminary experiments, the limit of detection for TNT under the above-mentioned conditions was 50 ng/ml. Various parameters such as flow rate, antibody density, and injection volume were not optimized. But, it was demonstrated that small i.d. capillaries (0.05 mm i.d.) can be used for the continuous flow immunoassay. Such small i.d. capillaries are very flexible and can be packaged into a small portable unit.

Example 9

Continuous Flow Immunoassay on a Chip.

Figure 9:
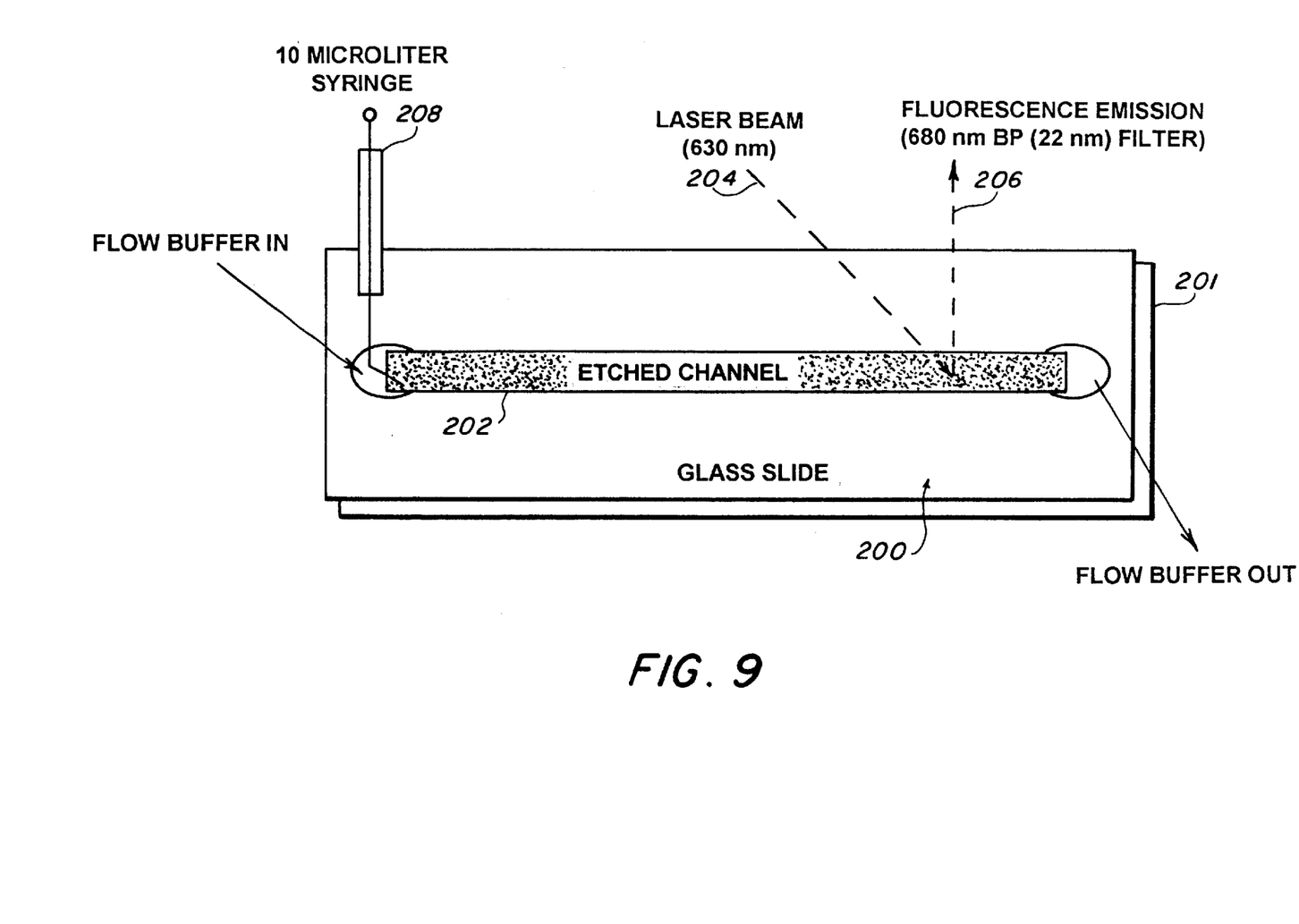
FIG. 9 is a simplified schematic representing a continuous flow immunoassay on a chip.

Preliminary experiments demonstrate the feasibility of the continuous flow immunoassay in a chip format. The experimental set up is shown in FIG. 9. Glass slides 200, 201 were etched to form a 5 cm long, 250 μm wide, and 80 μm deep channel (not shown) on each. This was followed by fusing slides 200 and 201 such that the on either slide formed a closed path 202. Anti-TNT antibody/Cy5-TNB complex (not shown) was immobilized onto the walls of path 202 using the same protocol as used for the capillaries. Online detection at the end of etched path was achieved using,the set up described by Jed Harrison et al., *Science*, 1993, 261, 895–896; Harrison et al., *Sensors and Actuators B*, 1996, 33, 105–109. A 630 nm laser beam 204 (2.5 mW output) was made incident on the etched path at a 45° angle from the plane of the glass chip. A 682±11 nm band pass filter and a PMT (not shown) placed at 90° from the plane of the chip were used to collect the fluorescence signal 206.

To perform an assay, flow buffer was continuously flowed through path 202 at a flow rate of approximately 20 μl/min. 1μl injections of TNT solutions (concentration ranging from 50 pg/ml–1000 ng/ml) were made into the etched path of the chip using a 10 μl syringe 208. A lower limit of detection of 220 attomoles of TNT (1 μl of 50 pg/ml TNT solution) was observed under these conditions. This system by no means was optimized but the proof of principle that such an immunoassay can be performed on a chip format is established.

Obviously, many modifications and variations of the present invention are possible in light of the above teachings. It is therefore to be understood that, within the scope of the appended claims, the invention may be practiced otherwise than as specifically described.

What is claimed is:

1. A flow-through immunosensor comprising:

an entrance port for receiving a fluid buffer, said entrance port being machined in or molded and integrated with a monolithic substrate;

a microcapillary passage machined in or molded and integrated with said monolithic substrate, said microcapillary passage having an inner diameter of less than about 1 mm and having antibodies immobilized on its inner wall, fluorescently labeled analogs of an antigen being immunologically bound to and saturating antigen-binding sites of said immobilized antibodies;

a sample introduction port in fluid connection with said microcapillary passage;

a detection cell downstream from and in fluid connection to said sample introduction port and joined to said microcapillary passage, said detection cell including;

at least one window transparent to a wavelength of light that fluorescently excites said label, and at least one window transparent to a wavelength of light emitted by said excited label; and an exit port machined in and integral with said monolithic substrate, said exit port being downstream from and in fluid connection with said detection cell, said exit port providing a path for spent buffer and label to exit said monolithic substrate.

2. The flow-through immunosensor of claim 1, wherein said immunosensor further includes an electroosmotic pump that establishes buffer flow through said microcapillary passage, said electroosmotic pump being integral with said monolithic substrate.

3. The flow-through immunosensor of claim 1, wherein said immunosensor further includes a pneumatic pump that establishes buffer flow through said microcapillary passage.

4. The flow-through immunosensor of claim 1, wherein said immunosensor further includes a mechanical pump that establishes buffer flow through said microcapillary passage.

5. The flow-through immunosensor of claim 2 or 3 or 4, wherein said buffer flow has a linear flow velocity of about no more than about 105 cm/min.

6. A method of performing a displacement assay using a flow-through immunosensor, comprising the steps of:

establishing a buffer flow through a microcapillary having an inner diameter of less than about 1 mm, said microcapillary passage having antibodies immobilized on its inner wall, and labeled analogs of an antigen immunologically bound to, and saturating antigen-binding sites of, said immobilized antibodies;

introducing a liquid sample, said sample being suspected of containing said antigen, into an introduction port in said microcapillary passage;

detecting, downstream from said introduction port and joined to said microcapillary passage, any of said bound labeled analogs displaced from said microcapillary passage by any molecules of said antigen present in said sample, wherein:

said bound labeled antigen is fluorescently labeled;

said microcapillary passage is machined or molded and integrated with said monolithic substrate;

said detecting step is carried out in a detection cell that is machined in or molded and integrated with said monolithic substrate, said detection cell including at least one window transparent to a wavelength of light that fluorescently excites said label, and at least one window transparent to a wavelength of light emitted by said excited label; and an exit port is machined in or molded and integral with said monolithic substrate, said exit port being downstream from and in fluid connection with said detection cell, said exit port providing a path for spent buffer and label to exit said monolithic substrate.

7. The method of claim 6, wherein said buffer flow is established by an electroosmotic pump that is integral with said monolithic substrate.

8. The method of claim 6, wherein said buffer flow is established by a pneumatic pump.

9. The method of claim 6, wherein said buffer flow is established by a mechanical pump.

* * * * *